United States Patent [19]

Koeda et al.

[11] 4,198,416
[45] Apr. 15, 1980

[54] 5-ALKOXY-PICOLINIC ESTERS AND ANTI-HYPERTENSIVE COMPOSITION CONTAINING 5-ALKOXY-PICOLINIC ESTERS

[75] Inventors: Takemi Koeda, Yokohama; Takashi Tsuruoka, Kawasaki; Uichi Shibata, Tokyo; Hiroyasu Asaoka, Yokohama; Mitsugu Hachisu, Kawasaki; Osamu Itoh; Yasuharu Sekizawa, both of Tokyo; Shigeharu Inouye, Kanagawa; Taro Niida, Yokohama, all of Japan

[73] Assignee: Meiji Seika Kaisha, Ltd., Tokyo, Japan

[21] Appl. No.: 944,683

[22] Filed: Sep. 22, 1978

Related U.S. Application Data

[63] Continuation-in-part of Ser. No. 838,180, Sep. 30, 1977.

[30] Foreign Application Priority Data

Sep. 30, 1976 [JP] Japan .................................. 51-116641

[51] Int. Cl.² .................... A61K 31/44; C07D 213/79
[52] U.S. Cl. ................................... 424/266; 546/269; 546/298
[58] Field of Search ................. 546/269, 298; 424/266

[56] References Cited

U.S. PATENT DOCUMENTS

| | | | |
|---|---|---|---|
| 3,519,717 | 7/1970 | Symchowicz et al. | 546/298 X |
| 3,737,542 | 6/1973 | Carlsson et al. | 546/318 X |
| 3,914,239 | 10/1975 | Kuhnis et al. | 546/301 X |
| 4,046,553 | 9/1977 | Takahashi et al. | 546/302 X |

OTHER PUBLICATIONS

Beyerman, Chemical Abstracts, vol. 52 (1958), 15529f.
Deady et al., Chemical Abstracts, vol. 74 (1971), 76278v.

*Primary Examiner*—Richard Raymond
*Attorney, Agent, or Firm*—Sughrue, Rothwell, Mion, Zinn and Macpeak

[57] ABSTRACT

5-Alkoxy-picolinic esters represented by the formula (I):

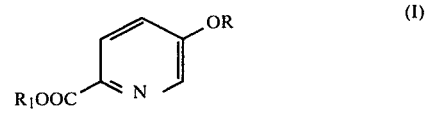

wherein R represents an alkyl group having 1 to 6 carbon atoms and $R_1$ represents an unsubstituted phenyl group; a phenyl group substituted with one or more of an alkyl group having 1 to 4 carbon atoms or an acetyl group; a phthalidyl group; an alkoxyalkyl group wherein the alkyl moiety and the alkoxy moiety each has 1 to 4 carbon atoms; an alkoxyalkoxyalkyl group wherein the alkyl moiety and the alkoxy moiety each has 1 to 4 carbon atoms; an indanyl group; or an acyloxyalkyl group having the formula

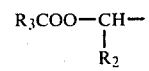

wherein $R_2$ represents a hydrogen atom or a methyl group and $R_3$ represents an alkyl group having 1 to 5 carbon atoms (such as a methyl, n-propyl, isobutyl, t-butyl, etc., group), an alkoxy group having 1 to 4 carbon atoms, a phenyl group, a phenyl group substituted with one or more of an alkyl group having 1 to 4 carbon atoms, an alkoxy group having 1 to 4 carbon atoms or a halogen atom (such as chlorine, bromine, iodine, etc., atom) or an aralkyl group wherein the alkyl moiety has 1 to 3 carbon atoms, which are useful as anti-hypertensive agents, a process for preparing 5-alkoxy-picolinic esters, and anti-hypertensive compositions containing the 5-alkoxy-picolinic esters.

10 Claims, No Drawings

5-ALKOXY-PICOLINIC ESTERS AND ANTI-HYPERTENSIVE COMPOSITION CONTAINING 5-ALKOXY-PICOLINIC ESTERS

CROSS-REFERENCE TO RELATED APPLICATIONS

This application is a continuation-in-part application of U.S. patent application Ser. No. 838,180, filed Sept. 30, 1977.

BACKGROUND OF THE INVENTION

1. Field of the Invention

This invention relates to new and useful compounds, 5-alkoxy-picolinic esters, to a process for preparing the same, and to pharmaceutical compositions containing the same.

2. Description of the Prior Art

It is known that hypertension often induces apoplexy, heart trouble, etc., which necessitates extensive research for new and useful anti-hypertensives.

Fusaric acid (5-n-butylpicolinic acid) is known to be useful as an anti-hypertensive agent as disclosed in *Jap. J. Pharmacol.*, Vol. 25, 188 (1975), however, fusaric acid has a butyl group at the 5-position of the picolinic acid moiety and has a low $LD_{50}$ value. As a result, an improved antihypertensive agent is desired.

British Patent No. 1,502,055 discloses that 3-substituted-2(1H)-pyridone-6-carboxylic acid can be used as an anti-hypertensive agent but the anti-hypertensive activity (i.e., maximum depression in blood pressure) thereof is poor and an improvement is desired.

SUMMARY OF THE INVENTION

As a result of extensive research, it has been found that 5-hydroxy-2-hydroxymethyl pyridine (e.g., as disclosed in *Tetrahedron*, Vol. 20, 2125 (1968)) obtainable easily from nojirimycin (e.g., as disclosed in Japanese Patent Publication No. 760/1968) provides useful compounds, 5-alkoxy-picolinic esters having excellent anti-hypertensive activity and low toxicity, and have succeeded in providing a new anti-hypertensive agent.

Accordingly, the present invention in one embodiment provides 5-alkoxy-picolinic esters represented by the formula (I):

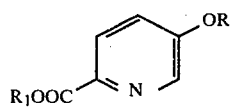

(I)

wherein R represents an alkyl group having 1 to 6 carbon atoms and $R_1$ represents an unsubstituted phenyl group; a phenyl group substituted with one or more of an alkyl group having 1 to 4 carbon atoms or an acetyl group; a phthalidyl group; an indanyl group; an alkoxyalkyl group wherein the alkyl moiety and the alkoxy moiety each has 1 to 4 carbon atoms; an alkoxyalkoxyalkyl group wherein the alkyl moiety and the alkoxy moiety each has 1 to 4 carbon atoms; or an acyloxyalkyl group having the formula

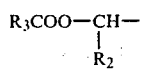

wherein $R_2$ represents a hydrogen atoms or a methyl group and $R_3$ represents an alkyl group having 1 to 5 carbon atoms (such as a methyl, n-propyl, isobutyl, t-butyl, etc., group), an alkoxy group having 1 to 4 carbon atoms, a phenyl group, a phenyl group substituted with one or more of an alkyl group having 1 to 4 carbon atoms, an alkoxy group having 1 to 4 carbon atoms or a halogen atom (such as a chlorine, bromine, iodine, etc., atom) or an aralkyl group wherein the alkyl moiety has 1 to 3 carbon atoms.

In another embodiment of this invention, this invention provides a process for preparing an ester of 5-alkoxy-picolinic acid represented by the fomula (I):

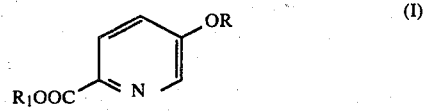

(I)

wherein R represents an alkyl group having 1 to 6 carbon atoms and $R_1$ represents an alkoxyalkyl group wherein the alkyl moiety and the alkoxy moiety each has 1 to 4 carbon atoms; an alkoxyalkoxyalkyl group wherein the alkyl moiety and the alkoxy moiety each has 1 to 4 carbon atoms; a phthalidyl group; or an acyloxyalkyl group having the formula

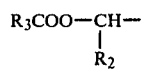

wherein $R_2$ represents a hydrogen atom or a methyl group and $R_3$ represents an alkyl group having 1 to 5 carbon atoms, an alkoxy group having 1 to 4 carbon atoms, an unsubstituted phenyl group, a phenyl group substituted with one or more of an alkyl group having 1 to 4 carbon atoms, an alkoxy group having 1 to 4 carbon atoms or a halogen atoms or an aralkyl group wherein the alkylmoiety has 1 to 3 carbon atoms, which comprises reacting a 5-alkoxy-picolinic acid or a salt thereof represented by the formula (II):

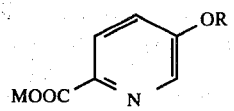

(II)

wherein R is as described above and M represents a hydrogen atom, a calcium atom, a sodium atom, a potassium atom or an aluminum atom, with an alkoxyalkyl halide wherein the alkoxy moiety and the alkyl moiety each has 1 to 4 carbon atoms; an alkoxyalkoxyalkyl halide wherein the alkyl moiety and the alkoxy moiety each has 1 to 4 carbon atoms; a 3-bromophthalide; or an acyloxyalkyl halide represented by the formula (III):

(III)

wherein X represents a halogen atom; $R_2$ represents a hydrogen atom or a methyl group and $R_3$ represents an alkyl group having 1 to 5 carbon atoms, an alkoxy group having 1 to 4 carbon atoms, an unsubstituted phenyl group, a phenyl group substituted with one or more of an alkyl group having 1 to 4 carbon atoms, an alkoxy group having 1 to 4 carbon atoms or a halogen atom or an aralkyl group wherein the alkyl moiety has 1 to 3 carbon atoms, in an organic solvent in the present of a base.

In even another embodiment of this invention, this invention provides a process for preparing an ester of 5alkoxy-picolinic acid represented by the formula (I):

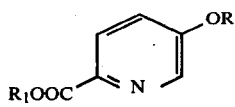 (I)

wherein R represents an alkyl group having 1 to 6 carbon atoms and $R_1$ represents an indanyl group, an unsubstituted phenyl group, or a phenyl group substituted with one or more of an alkyl group having 1 to 4 carbon atoms or an acetyl group; which comprises condensing a 5-alkoxy-picolinic acid represented by the formula (IV):

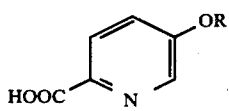 (IV)

wherein R is as described above, with a 5-hydroxyindane (i.e., 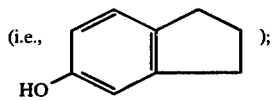 );

or a phenol or a substituted phenol represented by the formula (V):

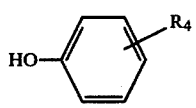 (V)

wherein $R_4$ represents a hydrogen atom, an alkyl group having 1 to 4 carbon atoms or an acetyl group, in an organic solvent in the presence of a dehydrating agent.

Also, an embodiment of this invention provides a process for preparing an ester of 5-alkoxy-picolinic acid represented by the formula (I):

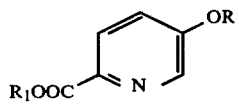 (I)

wherein R represents an alkyl group having 1 to 6 carbon atoms and $R_1$ represents an acyloxyalkyl group having the formula

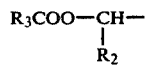

wherein $R_2$ represents a hydrogen atom or a methyl group and $R_3$ represents an alkyl group having 1 to 5 carbon atoms, an alkoxy group having 1 to 4 carbon atoms, an unsubstituted phenyl group, a phenyl group substituted with one or more of an alkyl group having 1 to 4 carbon atoms, an alkoxy group having 1 to 4 carbon atoms or a halogen atom or an aralkyl group wherein the alkyl moiety has 1 to 3 carbon atoms, which comprises reacting a 5-alkoxy-picolinic acid represented by the formula (IV):

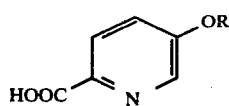 (IV)

wherein R represents an alkyl group having 1 to 6 carbon atoms, with an acid halogenating agent to produce an acid halide represented by the formula (VI):

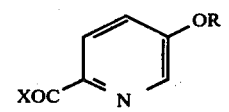 (VI)

wherein R is the same as defined above and X represents a halogen atom, and further reacting the acid halide of 5-alkoxy-picolinic acid represented by the formula (VI) above with an acyloxyalkanol represented by the formula (VII):

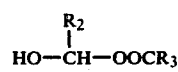 (VII)

wherein $R_2$ represents a hydrogen atom or a methyl group and $R_3$ represents an alkyl group having 1 to 5 carbon atoms, an alkoxy group having 1 to 4 carbon atoms, an unsubstituted phenyl group, a phenyl group substituted with one or more of an alkyl group having 1 to 4 carbon atoms, an alkoxy group having 1 to 4 carbon atoms or a halogen atom or an aralkyl group wherein the alkyl moiety has 1 to 3 carbon atoms, in an organic solvent in the presence of a base.

Also, an additional embodiment of this invention provides a process for preparing an ester of 5-alkoxy-picolinic acid represented by the formula (I):

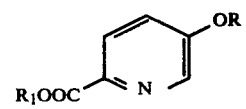 (I)

wherein R represents an alkyl group having 1 to 6 carbon atoms and $R_1$ represents an indanyl group, an unsubstituted phenyl group or a phenyl group substituted with one or more of an alkyl group having 1 to 4 carbon atoms or an acetyl group; which comprises reacting an acid halide of 5-alkoxy-picolinic acid represented by the formula (VI):

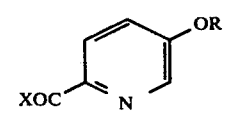 (VI)

wherein R is the same as defined above and X represents a halogen atom, with 5-hydroxyindane or a metal salt thereof, or a phenol, a substituted phenol or a metal salt thereof represented by the formula (VIII):

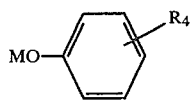

(VIII)

wherein R₄ represents a hydrogen atom, an alkyl group having 1 to 4 carbon atoms or an acetyl group and M represents a hydrogen atom, a metal atom (such as a calcium atom, a sodium atom, a potassium atom or an aluminum atom), in an organic solvent in the presence of a base.

In a further embodiment of this invention, this invention provides an anti-hypertensive composition containing, as an active ingredient, a therapeutically effective amount of at least one 5-alkoxy-picolinic ester having the formula (I) described above.

DETAILED DESCRIPTION OF THE INVENTION

The term "alkyl group having 1 to 6 carbon atoms" as used herein for R includes straight or branched chain alkyl groups and specific examples include methyl, ethyl, n-propyl, isopropyl, n-butyl, sec-butyl, tert-butyl, n-pentyl, n-hexyl and the like.

Suitable examples of $R_1$ in the formula (I) include an acyloxyalkyl group such as a pivaloyloxymethyl group, an α-pivaloyloxyethyl group, an acetoxymethyl group, an α-acetoxyethyl group, an α-propionyloxyethyl group, a benzoyloxymethyl group, an isobutyryloxymethyl group, an α-(isovaleroyloxy)ethyl group, an α-(benzoyloxy)ethyl group, an α-(p-methoxybenzoyloxy)ethyl group, an α-(3,4,5-trimethoxybenzoyloxy)ethyl group and an α-(ethoxycarbonyloxy)ethyl group; a phthalidyl group; an alkoxyalkyl group such as a methoxymethyl group; an alkoxyalkoxyalkyl group such as a methoxyethoxymethyl group; an indanyl group; and a phenyl group, such as a phenyl group, an ethylphenyl group and an acetylphenyl group.

More preferred examples of $R_1$ include a pivaloyloxymethyl group, an α-pivaloyloxyethyl group, an acetoxymethyl group, an isobutyryloxymethyl group, an α-(isovaleroyloxy)ethyl group, an α-benzoyloxyethyl group, an α-(3,4,5-trimethoxybenzoyloxy)ethyl group, a phthalidyl group, an indanyl group, a phenyl group, an ethylphenyl group and an acetylphenyl group.

Most preferred examples of $R_1$ include a pivaloyloxymethyl group, a phenyl group, an ethylphenyl group, an acetylphenyl group and an indanyl group.

The 5-alkoxy-picolinic acids of the formula (IV) wherein R represents an alkyl group having 1 to 6 carbon atoms used as a starting material to prepare the 5-alkoxy-picolinic esters of the formula (I) of this invention can be prepared by reacting 5-hydroxy-2-hydroxymethylpyridine of the formula (IX):

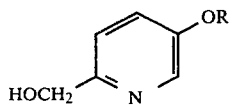

(IX)

with an alkyl halide of the formula (X):

RX    (X)

wherein R represents an alkyl group having 1 to 6 carbon atoms and X represents a halogen atom (such as bromine or chlorine), to obtain a 5-alkoxy-2-hydroxymethylpyridine of the formula (XI):

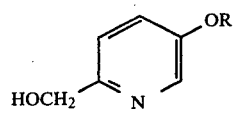

(XI)

wherein R is as defined above, and oxidizing the resulting 5-alkoxy-2-hydroxymethylpyridine of the formula (XI) with an oxidizing agent or a combination of oxidizing agents.

Alternatively, the compound of the formula (IV) above wherein R represents an alkyl group having 2 to 6 carbon atoms can also be prepared by reacting 5-hydroxy-2-hydroxymethylpyridine of the formula (IX) above with an alkenyl halide of the formula (X'):

R'X    (X')

wherein R' represents an alkenyl group having 2 to 6 carbon atoms (such as vinyl, allyl, 2-butenyl, 2-pentenyl, 2-hexenyl, etc.) and X represents a halogen atom (such as bromine or chlorine), to convert the hydroxyl group at the 5-position of the pyridine nucleus of the 5-hydroxy-2-hydroxymethylpyridine of the formula (IX) into an alkenyloxy group thereby producing a corresponding 5-alkenyloxy-2-hydroxymethylpyridine of the formula (XI'):

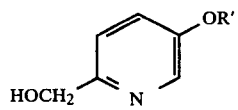

(XI')

wherein R' is as defined above, reducing the alkenyl group of the 5-alkenyloxy-2-hydroxymethylpyridine of the formula (XI') by hydrogenation to produce a corresponding 5-alkoxy-2-hydroxymethylpyridine of the formula (XI):

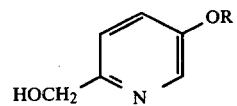

(XI)

wherein R represents an alkyl group having 2 to 6 carbon atoms, and oxidizing the resulting 5-alkoxy-2-hydroxymethylpyridine of the formula (XI) in the same manner as described above.

The process for the preparation of the compound of the formula (I) according to this invention is hereinafter described in detail.

In the process of this invention, the 5-hydroxy-2-hydroxymethylpyridine of the formula (IX), which can be prepared according to the disclosure in U.S. Pat. No. 2,944,059, can be reacted with an alkyl halide of the formula (X) in an organic solvent such as methanol, ethanol, acetone, dioxane, dimethylformamide, dimethyl sulfoxide, etc., at a temperature of about 20° to about 100° C., preferably 20° to 60° C., for a period of about 3 to about 35 hours, preferably 5 to 20 hours, to obtain a corresponding 5-alkoxy-2-hydroxymethylpyridine.

In the above reaction, the alkyl halide of the formula (X) can be used in an amount of from about 1 to about 5 mols, preferably 1.2 to 1.6 mols, per mol of 5-hydroxy-2-hydroxymethylpyridine of the formula (IX).

The reaction between the 5-hydroxy-2-hydroxymethylpyridine of the formula (IX) and the alkyl halide of the formula (X) can also be conducted in the presence of a base, e.g., an inorganic base such as sodium hydroxide, potassium hydroxide, sodium carbonate, potassium carbonate, sodium hydrogen carbonate or an organic base such as triethylamine, etc., as a hydrogen halide acceptor, either in water or in an aqueous organic solvent, for example, a mixture of water and an organic solvent as described above, e.g., in an amount of about 10 to about 50% by weight of water.

The base described above can be used in an amount of from about 1 to about 5 mols, preferably 1.2 to 1.6 mols, per mol of the 5-hydroxy-2-hydroxymethylpyridine of the formula (IX).

The reaction can be preferably conducted in dimethylformamide or dimethyl sulfoxide since the reaction proceeds most rapidly in such a solvent substantially without producing an N-alkylpyridinium salt as a by-product. In addition, the use of dimethylformamide or dimethyl sulfoxide as a solvent makes it possible to cause a highly selective replacement reaction of the hydroxyl group at the 5-position of the pyridine nucleus, whereby the reaction can be performed easily at a temperature from room temperature (about 15° to about 30° C.) to about 70° C. within a relatively short period of time, e.g., about 3 to about 8 hours. However, the other solvents described above can also be effectively used, although the selectivity of the replacement reaction at the 5-position is somewhat lower than that attainable by the use of dimethylformamide or dimethyl sulfoxide as the solvent. For example, when an alcohol is used as a solvent, a long reaction time is needed such as about 30 hours at 65° C. and about 30 mol% of an N-alkylpyridinium salt is produced as a by-product.

Alternatively, the intermediate, 5-alkoxy-2-hydroxymethylpyridine, represented by the formula (XI), can also be prepared by reacting 5-hydroxy-2-hydroxymethylpyridine with an alkenyl halide having 2 to 6 carbon atoms of the formula (X') in the same manner as described for the reaction between 5-hydroxy-2-hydroxymethylpyridine and the alkyl halide to obtain an alkenyloxy derivative of the formula (XI'). The alkenyl group of the resulting alkenyloxy derivative is then hydrogenated to produce an alkyl group in the presence of a catalyst such as palladium, platinum oxide, Raney nickel and the like in an organic solvent such as methanol, ethanol or dioxane.

The hydrogenation can be achieved in an atmosphere of hydrogen gas at atmospheric pressure to a pressure of about 5 atmospheres of hydrogen gas, preferably under atmospheric pressure, at a temperature of from about 20° to about 40° C., preferably at room temperature, for a period of about 0.5 to 3 hours, preferably 1 to 2 hours.

The catalyst for hydrogenation described above can be used in an amount of from about 3 to about 20% by weight, preferably 5 to 10%, based on the weight of the alkenyloxy derivative of the formula (XI').

The starting material used in preparing the compounds of this invention, the 5-alkoxy-picolinic acid of the formula (IV), can be derived from 5-alkoxy-2-hydroxymethylpyridine of the formula (XI) by reacting the latter with an oxidizing agent or a combination thereof such as potassium permanganate, chromic anhydride, potassium dichromate, selenium dioxide, nitric acid and the like in a suitable solvent such as water, sulfuric acid, acetic acid, pyridine, acetone or dioxane.

The oxidation can be achieved using about 1.2 to about 3 mols, preferably 1.5 to 2 mols, of the oxidizing agent per mol of the 5-alkoxy-2-hydroxymethylpyridine of the formula (XI) at a temperature of from about $-10°$ to about 80° C., preferably 5° to 30° C., for a period of from about 1 to about 25 hours, preferably 5 to 10 hours.

In an alternative oxidation procedure, the hydroxymethyl group at the 2-position of the 5-alkoxy-2-hydroxymethylpyridine of the formula (XI) can be first oxidized with a relatively mild oxidizing agent such as active manganese dioxide, e.g., in a molar ratio of about 5:1 to about 20:1 of the manganese dioxide to the compound of the formula (XI), at about 30° to about 80° C., to convert the hydroxymethyl group into a formyl group and produce a 5-alkoxy-2-formylpyridine compound. A suitable time for this oxidation can range from about 5 to 30 hours. The formyl group of the 5-alkoxy-2-formylpyridine compound is then oxidized into a carboxyl group with silver oxide or hydrogen peroxide at about 40° to about 80° C. A suitable amount of silver oxide which can be used is a molar ratio of about 1.2:1 to about 2:1 of the silver oxide to the 5-alkoxy-2-formylpyridine compound. A suitable time for this oxidation can range from about 1 to 5 hours.

In the above oxidation, a small amount of certain by-products is occasionally produced, but such by-products can be easily removed using conventional techniques such as solvent extraction, precipitation, crystallization and the like or a combination thereof.

The 5-alkoxy-picolinic acids thus-obtained may be converted into pharmaceutically acceptable inorganic salts such as the calcium, sodium, potassium or aluminum salts using well-known procedures. For example, such a conversion can be advantageously achieved by adding an alkali metal hydroxide, such as sodium hydroxide, potassium hydroxide and the like, to a solution or suspension of a 5-alkoxy-picolinic acid of the formula (IV) in a solvent such as water at a temperature of about 15° C. to about 30° C. such that the pH of the solution is about 7. The corresponding calcium and aluminum salts can be prepared from the sodium or potassium salts using calcium and aluminum salts such as calcium acetate monohydrate and aluminum sulfate, respectively.

The 5-alkoxy-picolinic acids of the formula (IV) produced as described above are then converted into the pharmaceutically acceptable esters such as the pivaloyloxymethyl ester, acetoxymethyl ester, phthalidyl ester, etc., using well-known procedures. For example, such a conversion can be achieved (1) by reacting an acyloxyalkyl halide (such as chloromethyl acetate, chloromethyl pivalate, α-chloroethyl pivalate, α-bromoethyl benzoate, chloroethyl p-methoxy benzoate, bromomethyl butyrate, etc.), an alkoxyalkyl halide or 3-bromophthalide with a 5-alkoxy-picolinic acid of the formula (IV), e.g., in a molar proportion of about 1:1.2 to about 1:2 of the 5-alkoxy-picolinic acid to the acyloxyalkyl halide, alkoxyalkyl halide or 3-bromophthalide, in a solvent such as dimethylformamide in the presence of a base, or (2) by condensing a 5-hydroxyindane, a phenol or a substituted phenol and a 5-alkoxy-picolinic acid of the formula (IV) using a dehydrating agent (such as dicyclohexylcarbodiimide, etc.). A suitable reaction temperature for the acyloxyalkyl halide, an alkoxyalkyl halide or 3-bromophthalide with 5-alkoxy-picolinic acid ranges from about $-20°$ C. to about 80° C., preferably from room temperature (about 15° to 30° C.) to 50° C. and the reaction time is generally about 4 to about 20 hours. A suitable reaction temperature for the 5-hydroxyindane, the phenol or substituted phenol and the 5-alkoxy-picolinic acid ranges from about −10° C. to about 40° C. and the reaction time generally ranges from about 3 to about 10 hours.

The organic esters of 5-alkoxy-picolinic acids of the formula (I) above wherein R represents an alkyl group having 1 to 6 carbon atoms and $R_1$ represents an indanyl group; an unsubstituted phenyl group; a phenyl group substituted with one or more of an alkyl group having 1 to 4 carbon atoms or an acetyl group; a phthalidyl group; an alkoxyalkyl group wherein the alkyl moiety and the alkoxy moiety each has 1 to 4 carbon atoms; an alkoxyalkoxyalkyl group wherein the alkyl moiety and the alkoxy moiety each has 1 to 4 carbon atoms; or an acyloxyalkyl group having the formula

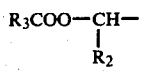

wherein $R_2$ represents a hydrogen atom or a methyl group and $R_3$ represents an alkyl group having 1 to 5 carbon atoms (such as a methyl, n-propyl, isobutyl, t-butyl, etc., group), an alkoxy group having 1 to 4 carbon atoms, a phenyl group, a phenyl group substituted with one or more of an alkyl group having 1 to 4 carbon atoms, an alkoxy group having 1 to 4 carbon atoms or a halogen atom (such as a chlorine, bromine, iodine, etc., atom) or an aralkyl group wherein the alkyl moiety has 1 to 3 carbon atoms, can be prepared, depending on the substituent $R_1$, by (a) reacting a 5-alkoxy-picolinic acid or a salt thereof represented by the formula (II):

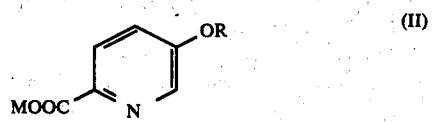

wherein R represents an alkyl group having 1 to 6 carbon atoms and M represents a hydrogen atom, a calcium atom, a sodium atom, a potassium atom or an aluminum atom, with an alkoxyalkyl halide wherein the alkoxy moiety and the alkyl moiety each has 1 to 4 carbon atoms; an alkoxyalkoxyalkyl halide wherein the alkyl moiety and the alkoxy moiety each has 1 to 4 carbon atoms; a 3-bromophthalide; or an acyloxyalkyl halide represented by the formula (III):

wherein X represents a halogen atom (e.g., as described above), $R_2$ represents a hydrogen atom or a methyl group and $R_3$ represents an alkyl group having 1 to 5 carbon atoms, an alkoxy group having 1 to 4 carbon atoms, an unsubstituted phenyl group, a phenyl group substituted with one or more of an alkyl group having 1 to 4 carbon atoms, an alkoxy group having 1 to 4 carbon atoms or a halogen atom or an aralkyl group wherein the alkyl moiety has 1 to 3 carbon atoms, in an organic solvent (such as dimethylformamide, dimethyl sulfoxide, etc.) in the presence of a base (such as triethylamine, pyridine, etc.), with a suitable reaction temperature ranging from about −20° C. to about 80° C. and the reaction time generally ranging from about 4 hours to about 20 hours;

(b) condensing a 5-alkoxy-picolinic acid represented by the formula (IV):

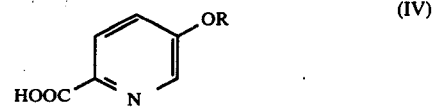

wherein R represents an alkyl group having 1 to 6 carbon atoms;

with 5-hydroxyindane; or a phenol or a substituted phenol represented by the formula (V):

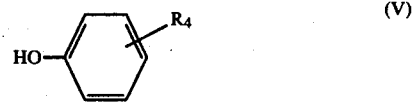

wherein $R_4$ represents a hydrogen atom, an alkyl group having 1 to 4 carbon atoms or an acetyl group, in an organic solvent (such as chloroform, dioxane, dimethylformamide, pyridine and the like) in the presence of a dehydrating agent (such as dicyclohexylcarbodiimide, etc.), with a suitable reaction temperature ranging from about 0° C. to about 40° C. and the reaction time generally ranging from about 3 to 10 hours;

(c) reacting a 5-alkoxy-picolinic acid represented by the formula (IV):

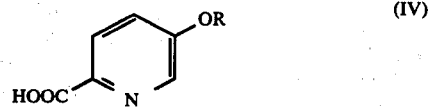

wherein R represents an alkyl group having 1 to 6 carbon atoms, with an acid halogenating agent (such as phosphorous trichloride, phosphorous tribromide, thionyl chloride, etc.) to produce an acid halide represented by the formula (VI):

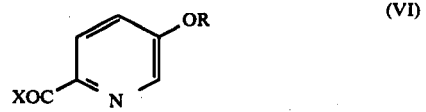

wherein R is the same as defined above and X represents a halogen atom (e.g., as described above), and further reacting the acid halide of 5-alkoxy-picolinic acid represented by the formula (VI) above with an acyloxyalkanol represented by the formula (VII):

wherein $R_2$ and $R_3$ are the same as defined in the formula (III) above, in an organic solvent (such as benzene, chloroform, methylene chloride, dimethylformamide, dioxane, etc.) in the presence of a base (such as pyridine, triethylamine), with a suitable reaction temperature ranging from about −20° C. to about 50° C. and the reaction time generally ranging from about 1 hour to about 10 hours; or (d) reacting an acid halide of 5-alkoxy-picolinic acid represented by the formula (VI) above, with a 5-hydroxyindane or a metal salt thereof; or a phenol, a substituted phenol or a metal salt thereof represented by the formula (VIII):

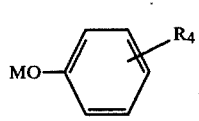 (VIII)

wherein $R_4$ represents a hydrogen atom, an alkyl group having 1 to 4 carbon atoms or an acetyl group and M represents a hydrogen atom, a calcium atom, a sodium atom, a potassium atom or an aluminum atom, in an organic solvent (such as chloroform, methylene chloride, dimethylformamide, dioxane, diethyl ether, benzene, etc.) in the presence of a base (such as pyridine, triethylamine, etc.), with a suitable reaction temperature ranging from about $-10°$ C. to about $40°$ C. and the reaction time generally ranging from about 3 hours to about 10 hours.

All the compounds of this invention represented by the formula (I) above exhibit a long-lasting anti-hypertensive activity by oral administration and can be regarded as useful pharmaceutical agents as illustrated in the Example 13 given hereinafter.

It is a known fact that the (hypertensive) activity of anti-hypertensive drugs is caused more or less by the dilating effect on blood vessels. Therefore, the compounds of the present invention may be used not only as an anti-hypertensive agent, but as a vasodilator agent, in particular, against peripheral vascular disease.

In general, the compounds of this invention may be administered orally in the form of tablets, capsules or a granular association, with usual pharmaceutical carriers, excipients or diluents. Suitable excipients which can be used include, e.g., calcium phosphate, sodium citrate, glycine, lactose, etc., and additionally binding agents (such as gelatin, gum arabic, polyvinyl pyrrolidone, etc.), lubricants (such as silica, magnesium stearate, etc.), disintegrating agents (such as starch, etc.), wetting agents (such as sodium lauryl sulfate, etc.) can be employed with the compound of this invention in the form of tablets or capsules.

The compound of this invention can be administered orally in the form of an aqueous suspension, an oily suspension, a solution, an emulsion, a syrup and an elixir. Suspending agents (such as methyl cellulose, gelatin, aluminum stearate gel, etc.), emulsifying agents (such as lecithin, sorbitan monooleate, gum arabic, etc.), diluents (such as almond oil, peanut oil, propylene glycol, ethyl alcohol, etc.), preservatives (such as methyl p-hydroxybenzoate, sorbic acid, etc.), sweeteners and flavorings can also be included in the aqueous suspension, oily suspension, solution, emulsion, syrup and elixir.

The compounds of this invention can also be administered in the form of a subcutaneous injection, for example, in the form of a suspension, a solution and an emulsion (e.g., using an oily vehicle or an aqueous vehicle). Usual additives, such as suspending agents, stabilizing agents, dispersing agents, and preservatives, can be included in the suspension, solution and emulsion. The compounds of this invention can also be administered in the form of a suppository containing cocoa butter or glycerides as a carrier.

The esters of the compounds of this invention are not soluble in water and, therefore, they are preferably orally administered, in general. However, the methods of administration of the compounds of this invention are not limited only to the method described above.

A suitable dosage amount of the compounds of this invention generally is about 150 mg to about 900 mg per day for an adult and the compounds of this invention can be administered daily in a single dose or in multiple doses such as two times to four times per day. An appropriate dosage amount is decided according to the age and the body weight of the patient, the condition of the disease and the dose amount and the kind of other medicines which are used together with the compounds of this invention.

The 5-alkoxy-picolinic esters of this invention can be used as the sole active agent or can be used in combination with one or more other therapeutically active agents. Especially, in hypertension therapy, different anti-hypertensive agents having different anti-hypertension activities are usually used in combination. The compounds of this invention can be used in combination with other anti-hypertensive agents, for example, thiazide-type diuretic anti-hypertensive agents.

This invention will be illustrated in greater detail by reference to the following Examples, but they are not to be considered as limiting the present invention. Unless otherwise indicated, all percents, parts, ratios, and the like are by weight.

REFERENCE EXAMPLE 1

4.48 g of potassium hydroxide was dissolved in a suspension of 10 g of 5-hydroxy-2-hydroxymethylpyridine in 100 ml of water, and the resulting solution was concentrated and dried to obtain the potassium salt of 5-hydroxy-2-hydroxymethylpyridine. The potassium salt thus-obtained was dried in a desiccator and suspended in 200 ml of dimethylformamide. 10.5 g of n-propylbromide was added to the suspension which was then stirred at 60° C. for 8 hours to effect the reaction. The reaction solution was concentrated under reduced pressure, and the resulting dry material was mixed with 200 ml of chloroform and 200 ml of water and two layers formed. The chloroform layer was separated and dried with anhydrous sodium sulfate followed immediately by concentration to obtain 9.8 g of a syrup of 5-n-propyloxy-2-hydroxymethylpyridine. The unreacted materials were found to remain in the aqueous layer. Thin layer chromatography (silica gel) of the thus-obtained product using a solvent system of chloroform-methanol (5:1 by volume) showed a single spot of an $R_f$ of 0.7.

| Elemental Analysis for $C_6H_{13}NO_2$: | | | |
|---|---|---|---|
| | C | H | N |
| Calculated (%): | 64.67 | 7.78 | 8.38 |
| Found (%): | 64.71 | 7.68 | 8.42 |

Mass Spectral Analysis: M+167

5 g of the above 5-n-propyloxy-2-hydroxymethylpyridine was dissolved in 200 ml of acetone, and 14 g of potassium permanganate was added to the solution over a 2 hour period while stirring the mixture at 40° C. The reaction was further continued for 1 hour at 40° C. and then the reaction solution was immediately concentrated to dryness. 200 ml of a 0.1 N aqueous potassium hydroxide solution was then added to the residue while stirring the mixture, followed by filtration of the mixture. The resulting filtrate was adjusted to a pH of 1.5 with a 5 N aqueous hydrochloric acid solution, and then extracted with 300 ml of chloroform. The chloroform extract was dried with anhydrous sodium sulfate and concentrated to a volume of about 10 ml. 30 ml of ethanol was then added to the concentrate, the mixture was allowed to stand and the product crystallized. The crystals thus-obtained were separated by filtration and dried in a desiccator to obtain 4.2 g of white needle crystals of 5-n-propyloxy-picolinic acid.
Melting Point: 128°–130° C.

| Elemental Analysis for $C_9H_{11}NO_3$: | | | |
|---|---|---|---|
| | C | H | N |
| Calculated (%): | 59.67 | 6.08 | 7.73 |
| Found (%): | 59.70 | 6.18 | 7.67 |

REFERENCE EXAMPLE 2

5 g of 5-hydroxy-2-hydroxymethylpyridine was suspended in 30 ml of methanol, and 2.16 g of sodium methoxide was added to the suspension. 60 ml of dimethyl sulfoxide was added to the mixture, and the resulting solution was then concentrated to evaporate the methanol. 5.7 g of n-butylbromide was added to the solution in dimethyl sulfoxide and stirred at 50° C. for 6 hours to effect the reaction. After evaporating off the solvent under reduced pressure, the resulting residue was mixed with 150 ml of chloroform and 100 ml of water and two phases separated. The unreacted materials were found to remain in the water layer. The chloroform layer was concentrated to obtain 4.8 g of a syrup of 5-n-butyloxy-2-hydroxymethylpyridine. Thin layer chromatography (silica gel) using a solvent system of chloroform-methanol (5:1 by volume) of the product showed a single spot of an $R_f$ of 0.72.

| Elemental Analysis for $C_{10}H_{15}NO_2$: | | | |
|---|---|---|---|
| | C | H | N |
| Calculated (%): | 66.30 | 8.29 | 7.73 |
| Found (%): | 66.23 | 8.35 | 7.67 |

Mass Spectral Analysis: M+181

4.5 g of the resulting compound was dissolved in 100 ml of dioxane, and 20 g of activated manganese dioxide was added to the solution followed by stirring the mixture at 60° C. for 14 hours to effect the reaction. The reaction solution was filtered while warm, and the filtrate was decolorized with activated carbon, followed by concentration to obtain 4.3 g of a syrup of 5-n-butyloxypyridine-2-carbaldehyde. Thin layer chromatography (silica gel) of this compound using a solvent system of chloroform-methanol (5:1 by volume) showed a single spot of an $R_f$ of 0.92.

2.9 g of the above compound was then dissolved in 50 ml of methanol, and the resulting solution was added to an aqueous alkaline solution of silver oxide which was prepared from 5 g of silver nitrate and 40 ml of a 2.5 N aqueous sodium hydroxide solution. The resulting mixture was stirred at 60° C. for 2 hours to effect the reaction. The reaction solution was filtered while warm, and the filtrate was washed with 50 ml of a 0.1 N aqueous solution of sodium hydroxide. The combined filtrate and washing was concentrated to about 50 ml, and the concentrate was adjusted to a pH of 1.5 with a 5 N aqueous hydrochloric acid solution followed by extraction with 100 ml of chloroform. The extract was washed with water and dried with anhydrous sodium sulfate, followed by concentration to about 3 ml. 5 ml of ethanol and 6 ml of diethyl ether were added to the concentrate, the mixture was allowed to stand at 3° C. and crystals were obtained. The crystals thus-obtained were filtered to obtain 2.3 g of white needle crystals of 5-n-butyloxy-picolinic acid.
Melting Point: 112°–114° C.

| Elemental Analysis for $C_{10}H_{13}NO_3$: | | | |
|---|---|---|---|
| | C | H | N |
| Calculated (%): | 61.54 | 6.67 | 7.18 |
| Found (%): | 61.73 | 6.54 | 7.21 |

REFERENCE EXAMPLE 3

8.85 g of 5-hydroxy-2-hydroxymethylpyridine was suspended in a mixture of 30 ml of water and 300 ml of acetone and 13.5 g of potassium carbonate was added to the suspension followed by stirring at 60° C. for 2 hours while adding dropwise thereto a solution of 10.5 g of allyl bromide in 80 ml of acetone. The reaction solution was further stirred for 2 hours to effect the reaction. The reaction solution was then rendered neutral with a 5 N aqueous hydrochloric acid solution and concentrated, followed by evaporation of any excess of the reagents.

300 ml of ethyl acetate and 200 ml of water were added to the residue and the mixture was then transferred into a separation funnel and stirred thoroughly. An N-allylpyridinium salt produced as a by-product remained in the aqueous layer. The ethyl acetate was concentrated to obtain 7.2 g of 5-allyloxy-2-hydroxymethylpyridine.

| Elemental Analysis for $C_9H_{11}NO_2$: | | | |
|---|---|---|---|
| | C | H | N |
| Calculated (%): | 65.45 | 6.67 | 8.48 |
| Found (%): | 65.38 | 6.70 | 8.42 |

Mass Spectral Analysis: M+165

The above compound was dissolved in 200 ml of ethanol, and the mixture was then subjected to a catalytic reduction with 200 mg of palladium black at room temperature and under atmospheric pressure. The reaction was completed within about 30 minutes. The catalyst was filtered from the reaction mixture and the filtrate was concentrated to dryness, which was then mixed with 300 ml of chloroform and 300 ml of water whereby 2 layers separated. The chloroform layer was concentrated to obtain 6.3 g of a syrup of 5-n-propyloxy-2-hydroxymethylpyridine. 5.0 g of this compound was dissolved in 30 ml of pyridine, to which was further added 9 g of selenium dioxide and the resulting mixture was stirred at 100° to 105° C. for 5 hours to effect the reaction. The selenium precipitated was separated from the reaction mixture by filtration and the filtrate was concentrated to dryness. 100 ml of water was added to the residue and the solution was adjusted to a pH of 9 with a 5 N aqueous sodium hydroxide solution and washed with 50 ml of chloroform. The aqueous layer was separated and adjusted to a pH of 1.5 with a 5 N aqueous hydrochloric acid solution. The mixture was extracted with 100 ml of chloroform, and the chloroform layer separated was decolorized with activated carbon. The chloroform layer was concentrated to about 10 ml, 20 ml of ethanol was added to the concentrate and crystals were obtained. Recrystallization from chloroform-ethanol (1.3 by volume) provided 4.2 g of white needle crystals of 5-n-propyloxy-picolinic acid.

REFERENCE EXAMPLE 4

1.6 g of sodium hydroxide was added to the suspension of 7.3 g of 5-n-propyloxy-picolinic acid in 300 ml water, and the mixture was stirred to obtain an aqueous solution of a sodium salt of the acid. 30 ml of an aqueous solution of 3.6 g of calcium acetate (monohydrate) was added dropwise to the above solution to obtain a precipitate. The resulting precipitate was filtered and washed with water, followed by drying in a desiccator, to obtain 8.1 g of a white powder of the calcium salt of 5-n-propyloxy-picolinic acid.
Melting Point: higher than 230° C.

Elemental Analysis for $C_9H_{10}NO_3 \cdot \frac{1}{2}Ca$

|  | C | H | N |
|---|---|---|---|
| Calculated (%): | 54.00 | 5.00 | 7.00 |
| Found (%): | 53.81 | 5.16 | 7.02 |

EXAMPLE 1

975 mg of 5-n-butyloxy-picolinic acid prepared as described in Reference Example 2 was dissolved in 20 ml of dimethylformamide and 1.5 g of chloromethylpivalate and 1.4 ml of triethylamine were added to the solution followed by stirring at room temperature for 6 hours. 10 ml of ice-water was added to the reaction solution followed by allowing the mixture to stand for 2 hours and then concentrated. 100 ml of ethyl acetate was added to the resulting residue and the solution was washed with 50 ml each of an acidic aqueous solution (adjusted to a pH of 2 with a 2 N aqueous hydrochloric acid solution), an alkaline aqueous solution (adjusted to a pH of 8.5 with a 2 N aqueous sodium hydroxide solution) and water. The ethyl acetate layer was then dried with anhydrous sodium sulfate followed by concentration and then dried under reduced pressure to obtain 1.38 g of an oil of the pivaloyloxymethyl ester of 5-n-butyloxy-picolinic acid. Thin layer chromatography (silica gel) of the thus-obtained product using a solvent system of benzene-acetone (10:1 by volume) showed a single spot of an $R_f$ 3.73.

Elemental Analysis for $C_{16}H_{23}NO_5$:

|  | C | H | N |
|---|---|---|---|
| Calculated (%): | 62.13 | 7.44 | 4.53 |
| Found (%): | 62.18 | 7.38 | 4.48 |

EXAMPLE 2

975 mg of 5-n-butyloxy-picolinic acid prepared as described in Reference Example 2 was dissolved in 25 ml of dimethylformamide. 1,010 mg of 3-bromophthalide was added to the solution and then 0.8 ml of triethylamine was further added thereto followed by stirring the mixture at room temperature for 5 hours. 5 ml of ice-water was added to the reaction solution followed by allowing the solution to stand for 2.5 hours. Then the solution was concentrated. 100 ml of ethyl acetate was added to the resulting residue and the solution was washed with 50 ml each of an acidic aqueous solution (adjusted to a pH of 2 with a 2 N aqueous hydrochloric acid solution), an alkaline aqueous solution (adjusted to a pH of 8.5 with a 2 N aqueous sodium hydroxide solution) and water. The ethyl acetate layer was then dried with anhydrous sodium sulfate and concentrated to a volume of about 15 ml. The concentrate was allowed to stand at 3° C. to obtain crystals. The crystals thus-obtained were filtered to obtain 1.22 g of crystals of the phthalidyl ester of 5-n-butyloxy-picolinic acid. Thin layer chromatography (silica gel) of the thus-obtained product using a solvent system of benzene-acetone (10:1 by volume) showed a single spot of an $R_f$ of 0.58.
Melting Point: 137°–138° C.

Elemental Analysis for $C_{18}H_{17}NO_5$:

|  | C | H | N |
|---|---|---|---|
| Calculated (%): | 66.05 | 5.20 | 4.28 |
| Found (%): | 66.08 | 5.17 | 4.26 |

EXAMPLE 3

835 mg of 5-n-propyloxy-picolinic acid prepared as described in Reference Example 1 was dissolved in 25 ml of dimethylformamide and, 850 mg of chloromethyl acetate and 1.3 ml of triethylamine were added to the solution followed by stirring the mixture at room temperature for 4 hours. Precipitated triethylamine hydrochloride was filtered out and the filtrate was concentrated to a volume of about 5 ml. 100 ml of ethyl acetate and 50 ml of water were added to the concentrate and, then, the mixture was adjusted to a pH of 8.5 with a 2 N aqueous sodium hydroxide solution and thereby unreacted compounds and dimethylformamide were transferred to the water layer. The ethyl acetate layer was separated and washed twice with 40 ml of water and dried with anhydrous sodium sulfate. The resulting ethyl acetate solution was concentrated and dried under reduced pressure to obtain 1.14 g of an oil of the acetoxymethyl ester of 5-n-propyloxy-picolinic acid. Thin layer chromatography (silica gel) of the thus-obtained product using a solvent system of benzene-acetone (10:1 by volume) showed a single spot of an $R_f$ of 0.43.

Elemental Analysis for $C_{12}H_{15}NO_5$:

|  | C | H | N |
|---|---|---|---|
| Calculated (%): | 56.92 | 5.93 | 5.53 |
| Found (%): | 57.01 | 5.90 | 5.51 |

EXAMPLE 4

975 mg of 5-n-butyloxy-picolinic acid prepared as described in Reference Example 2 was dissolved in 20 ml of dimethylformamide and 1.52 g of α-pivaloyloxyethyl chloride and 1.4 ml of triethylamine were added to the solution followed by stirring the mixture at room temperature for 20 hours. The same treatment as described in Example 3 above was conducted to obtain an ethyl acetate layer. The obtained ethyl acetate layer was concentrated to obtain a crystalline residue. Recrystallization from hexane gave 1.28 g of crystals of the α-pivaloyloxyethyl ester of 5-n-butyloxy-picolinic acid. Thin layer chromatography (silica gel) of the thus-obtained product using a solvent system of benzene-acetone (10:1 by volume) showed a single spot of an $R_f$ of 0.77.

Melting Point: 67°–68° C.

Elemental Analysis for $C_{17}H_{25}NO_5$:

|  | C | H | N |
|---|---|---|---|
| Calculated (%): | 63.16 | 7.74 | 4.33 |
| Found (%): | 63.12 | 7.76 | 4.35 |

EXAMPLE 5

835 mg of 5-n-propyloxy-picolinic acid prepared as described in Reference Example 1 was dissolved in 20 ml of dimethylformamide and 1.7 g of bromomethylisobutyrate and 1.3 ml of triethylamine was added to the solution followed by stirring at room temperature for 10 hours. 10 ml of ice-water was added to the reaction solution followed by allowing the mixture to stand for 2 hours. Then the mixture was concentrated. 100 ml of ethyl acetate was added to the resulting residue and the solution was washed with 50 ml each of an acidic aqueous solution (adjusted to a pH of 2 with a 2 N aqueous hydrochloric acid solution), an alkaline aqueous solution (adjusted to a pH of 8.5 with a 2 N aqueous sodium hydroxide solution) and water. The ethyl acetate layer was then dried with anhydrous sodium sulfate followed by concentration and then dried under reduced pressure to obtain 0.92 g of the isobutyryloxymethyl ester of 5-n-propyloxy-picolinic acid as an oil. Thin layer chromatography (silica gel) of the thus-obtained product using a solvent system of benzene-acetone (10:1 by volume) showed a single spot of an $R_f$ of 0.55.

Elemental Analysis for $C_{15}H_{21}O_5N$:

|  | C | H | N |
|---|---|---|---|
| Calculated (%): | 61.02 | 7.12 | 4.76 |
| Found (%): | 61.13 | 7.18 | 4.72 |

EXAMPLE 6

975 mg of 5-n-butyloxy-picolinic acid prepared as described in Reference Example 2 was dissolved in 30 ml of dimethylformamide and 1.8 g of α-chloroethylbenzoate and 1.4 ml of triethylamine were added to the solution followed by stirring the mixture at 35° C. for 15 hours. The precipitated triethylamine hydrochloride was filtered out and the filtrate was concentrated to a volume of about 5 ml. 100 ml of ethyl acetate and 50 ml of water were added to the concentrate and, then, the mixture was adjusted to a pH of 8.5 with a 2 N aqueous sodium hydroxide solution and thereby unreacted compounds and dimethylformamide were transferred to the water layer. The ethyl acetate layer was separated and washed twice with 40 ml of water and dried with anhydrous sodium sulfate. The resulting ethyl acetate solution was concentrated and dried under reduced pressure to obtain 1.14 g of the α-benzoyloxyethyl ester of 5-n-butyloxy-picolinic acid as an oil. Thin layer chromatography (silica gel) of the thus-obtained product using a solvent system of benzene-acetone (10:1 by volume) showed a single spot of an $R_f$ of 0.76.

Elemental Analysis for $C_{19}H_{21}O_5N$:

|  | C | H | N |
|---|---|---|---|
| Calculated (%): | 66.47 | 6.12 | 4.08 |
| Found (%): | 66.51 | 6.08 | 4.11 |

EXAMPLE 7

975 mg of 5-n-butyloxy-picolinic acid prepared as described in Reference Example 2 was dissolved in 30 ml of dimethylformamide and 1.65 g of α-(isovaleroyloxy)ethyl chloride and 1.4 ml of triethylamine were added to the solution followed by stirring the mixture at 40° C. for 15 hours. The same treatment as described in Example 1 above was conducted to obtain an ethyl acetate layer. The ethyl acetate layer obtained was concentrated and the residue was dissolved in 5 ml of hexane and allowed to stand at 3° C., and thereby, crystals were precipitated. After filtration, the crystals were dried under reduced pressure to obtain 920 mg of white crystals of the α-(isovaleroyloxy)ethyl ester of 5-n-butyloxy-picolinic acid. Thin layer chromatography (silica gel) of the thus-obtained product using a solvent system of benzene-acetone (10:1 by volume) showed a single spot of an $R_f$ of 0.78.

Melting Point: 54°–55° C.

Elemental Analysis for $C_{17}H_{25}O_5N$:

|  | C | H | N |
|---|---|---|---|
| Calculated (%): | 63.16 | 7.74 | 4.33 |
| Found (%): | 63.08 | 7.79 | 4.29 |

EXAMPLE 8

975 mg of 5-n-butyloxy-picolinic acid prepared as described in Reference Example 2 was dissolved in 20 ml of dimethylformamide and 2.0 g of α-(3,4,5-trimethoxybenzoyloxy)-ethyl chloride and 1.3 ml of triethylamine were added to the solution followed by stirring the mixture at 50° C. for 18 hours. The same treatment as described in Example 3 above was conducted to obtain an ethyl acetate layer. The ethyl acetate layer obtained was concentrated and 2.9 g of the residue was dissolved in 4 ml of benzene. The solution was column chromatographed (silica gel of 100 ml, filled with benzene) and eluted using a solvent mixture of benzene and acetone (30:1 volume ratio) to obtain 10 ml fractions. Fractions 30 to 62 were collected and concentrated and the residue was dissolved in 10 ml of diethyl ether. The solution was allowed to stand at 3° C. and, thereby, crystals were precipitated. After filtration, the crystals were dried under reduced pressure to obtain 2.1 g of crystals of the α-(3,4,5-trimethoxybenzoyloxy)ethyl ester of 5-n-butyloxy-picolinic acid. Thin layer chromatography (silica gel) of the thus-obtained product using a solvent system of benzene-acetone (10:1 by volume) showed a single spot of an $R_f$ of 0.61.

Melting Point: 80.0°–80.5° C.

Elemental Analysis for $C_{22}H_{27}O_8N$:

|  | C | H | N |
|---|---|---|---|
| Calculated (%): | 60.97 | 6.24 | 3.23 |
| Found (%): | 61.02 | 6.21 | 3.18 |

EXAMPLE 9

3 g of 5-n-butyloxy-picolinic acid prepared as described in Reference Example 2 was suspended in 30 ml of benzene and 8 ml of thionyl chloride was added to the suspension followed by stirring the mixture at 70° C. for 3 hours. The resulting solution was then concentrated to dryness. 10 ml of benzene was then added to the residue and the resulting solution was concentrated to dryness. The addition of the benzene (10 ml) and the concentration to dryness was further repeated two times so as to remove hydrogen chloride and sulfur dioxide by-produced and, thereby, the acid chloride of 5-n-butyloxy-picolinic acid (hydrochloride) was obtained.

1.2 g of the acid chloride obtained as described above was dissolved in 5 ml of benzene and, then, the resulting solution was added dropwise to a solution of 0.58 g of phenol, 2.5 ml of triethylamine and 10 ml of benzene for 10 minutes under cooling with ice-water while stirring. The solution was stirred for 2 hours at 5°–10° C. and further stirred for 2 hours at room temperature to complete the reaction. The reaction solution was then concentrated to dryness. 100 ml of ethyl acetate was then added to the residue and the resulting solution was washed with 50 ml of cooled (at 5° C.) hydrochloric acid aqueous solution (pH 2), 50 ml of alkaline aqueous solution of sodium bicarbonate (pH 9) and 50 ml of water, respectively. The ethyl acetate solution was dried over anhydrous sodium sulfate and, then, concentrated to dryness to obtain a crystalline residue. Recrystallization from diethyl ether-hexane provided 0.98 g of white needle-like crystals of the phenyl ester of 5-n-butyloxy-picolinic acid.

Melting Point 71°–72° C.

| Elemental Analysis for $C_{16}H_{17}NO_3$: | | | |
|---|---|---|---|
| | C | H | N |
| Calculated (%): | 70.85 | 6.27 | 5.17 |
| Found (%): | 71.03 | 6.14 | 5.21 |

EXAMPLE 10

1.1 g of the acid chloride of 5-n-butyloxy-picolinic acid (hydrochloride) obtained as described in Example 9 was dissolved in 10 ml of chloroform. The chloroform solution was added dropwise to a solution of 0.55 g of p-ethylphenol, 2.2 ml of triethylamine and 30 ml of chloroform under cooling with ice-water. The solution was stirred for 2 hours at 5° to 10° C. and further stirred for 3 hours at room temperature to complete the reaction. The reaction solution was washed with 20 ml of a cooled (at 5° C.) hydrochloric acid aqueous solution (pH 2), 20 ml of an alkaline aqueous solution of sodium bicarbonate (pH 9) and 20 ml of water, respectively. The chloroform layer was dried over anhydrous sodium sulfate and then concentrated to dryness to obtain a crystalline residue. Recrystallization from diethyl ether-hexane provided 0.92 g of white crystals of the p-ethylphenyl ester of 5-n-butyloxy-picolinic acid.

Melting Point: 67°–68° C.

| Elemental Analysis for $C_{18}H_{21}NO_3$: | | | |
|---|---|---|---|
| | C | H | N |
| Calculated (%): | 72.24 | 7.02 | 4.68 |
| Found (%): | 71.92 | 7.13 | 4.74 |

EXAMPLE 11

1.25 g of the acid chloride of 5-n-butyloxy-picolinic acid (hydrochloride) obtained as described in Example 9 was dissolved in 5 ml of dichloromethane and the dichloromethane solution was added dropwise to a solution of 0.69 g of p-hydroxyacetophenone, 2.5 ml of triethylamine and 20 ml of dichloromethane under cooling with ice-water. The solution was stirred for 1 hour at 3°–5° C. and further stirred for 3 hours at room temperature to complete the reaction. The reaction solution was washed with 20 ml of a cooled (at 5° C.) hydrochloric acid aqueous solution (pH 2), 20 ml of an alkaline aqueous solution of sodium bicarbonate (pH 9) and 20 ml of water, respectively. The dichloromethane layer was dried over anhydrous sodium sulfate and then concentrated to dryness to obtain a crystalline residue. Recrystallization from ethylacetate provided 0.75 g. of white crystals of the p-acetylphenyl ester of 5-n-butyloxy-picolinic acid.

Melting Point: 94°–96° C.

| Elemental Analysis for $C_{18}H_{19}NO_4$: | | | |
|---|---|---|---|
| | C | H | N |
| Calculated (%): | 69.01 | 6.07 | 4.47 |
| Found (%): | 69.17 | 6.01 | 4.50 |

EXAMPLE 12

3 g of 5-n-butyloxy-picolinic acid prepared as described in Reference Example 2 was suspended in 30 ml of benzene and 8 ml of thionyl chloride was added to the suspension followed by stirring the mixture at 70° C. for 3 hours. The resulting solution was then concentrated to dryness. 10 ml of benzene was then added to the residue and the resulting solution was concentrated to dryness. The addition of benzene (10 ml) and the concentration to dryness was further repeated two times so as to remove hydrogen chloride and sulfur dioxide by-produced and, thereby, the acid chloride of 5-n-butyloxy-picolinic acid (hydrochloride) was obtained. The acid chloride thus-obtained was dissolved in 20 ml of benzene and, then, the resulting solution was added dropwise to a solution of 2.1 g of 5-hydroxyindane, 7.7 ml of triethylamine and 30 ml of benzene for 10 minutes under cooling with ice-water while stirring. The solution was stirred for 1.5 hours at 5°–10° C. and further stirred for 4 hours at room temperature to complete the reaction. The reaction solution was then concentrated to dryness. 100 ml of ethyl acetate was then added to the residue and the resulting solution was washed with 50 ml of cooled (at 5° C.) hydrochloric acid solution (pH 2), 50 ml of alkaline aqueous solution of sodium bicarbonate (pH 9) and 50 ml of water, respectively. The ethyl acetate solution was dried over anhydrous sodium sulfate and, then, concentrated to dryness to obtain a crystalline residue. Recrystallization from diethylether-hexane provided 4.5 g of crystals of the 5-indanyl ester of 5-n-butyloxy-picolinic acid.

Melting Point: 58°–59° C.

Elemental Analysis for $C_{19}H_{21}NO_3$:

|  | C | H | N |
|---|---|---|---|
| Calculated (%): | 73.31 | 6.75 | 4.50 |
| Found (%): | 73.28 | 6.86 | 4.35 |

EXAMPLE 13

Each of the compounds indicated below was suspended in a 5% aqueous gum arabic solution containing 2% Tween 80, and the suspension was administered orally to groups of spontaneously hypertensive rats (SHR) (15–20 weeks old; 3 rats per group; blood pressure before administration: 175–190 mm Hg). Arterial blood pressure of concious SHR was recorded from the caudal artery via a pressure transducer (NIHON KOHDEN MP-24T) on a polygraph (NIHON KOHDEN RM-85).

The results obtained are shown in the table below.

| Test Compound | Dose (mg/kg) | Maximum Depression in Blood Pressure (%) |
|---|---|---|
| Pivaloyloxymethyl Ester of 5-n-Butyloxy-picolinic Acid | 100 | 17.5 |
| Acetoxymethyl Ester of 5-n-Propyloxy-picolinic Acid | " | 9.8 |
| Isobutyryloxymethyl Ester of 5-n-Butyloxy-picolinic Acid | " | 9.5 |
| Phenyl Ester of 5-n-Butyloxy-picolinic Acid | " | 20.0 |
| p-Ethylphenyl Ester of 5-n-Butyloxy-picolinic Acid | " | 18.7 |
| p-Acetylphenyl Ester of 5-n-Butyloxy-picolinic Acid | " | 15.4 |
| 5-Indanyl Ester of 5-n-Butyloxy-picolinic Acid | " | 21.8 |
| Fusaric Acid* (control) | " | 10.5 |

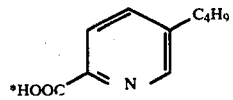

The oral $LD_{50}$ of the fusaric acid (control) was 180 mg/kg and the oral $LD_{50}$ of free 5-alkoxy-picolinic acids, such as 5-n-propyloxy-picolinic acid and 5-n-butyloxy-picolinic acid, was 300–500 mg/kg. On the other hand, the oral $LD_{50}$ of the esters of 5-alkoxy-picolinic acid of the present invention were improved, for example, 600–1,000 mg/kg for the acyloxyalkyl esters and the alkoxyalkyl esters, about 1,200 mg/kg for the phthalidyl ester, 600–800 mg/kg for the phenyl esters, higher than 800 mg/kg for the acetylphenyl ester and 800–1,000 mg/kg for the indanyl ester.

While the invention has been described in detail and with reference to specific embodiments thereof, it will be apparent to one skilled in the art that varuous changes and modifications can be made therein without departing from the spirit and scope thereof.

What is claimed is:

1. 5-Alkoxy-picolinic esters represented by the formula (I):

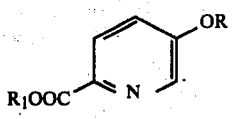

wherein R represents an alkyl group having 1 to 6 carbon atoms and $R_1$ represents a phthalidyl group; a phenyl group; an indanyl group; or an acyloxyalkyl group having the formula

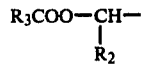

wherein $R_2$ represents a hydrogen atom or a methyl group and $R_3$ represents an alkyl group, an alkoxy group, a phenyl group or an aralkyl group.

2. The 5-alkoxy-picolinic esters according to claim 1, wherein $R_1$ represents a pivaloyloxymethyl group, an α-pivaloyloxyethyl group, an acetoxymethyl group, an α-acetoxyethyl group, an α-propionyloxyethyl group, a benzoyloxymethyl group, an isobutyryloxymethyl group, an α-(isovaleroyloxy) ethyl group, an α-(benzoyloxy) ethyl group, an α-(p-methoxybenzoyloxy)ethyl group, an α-(3,4,5-trimethoxybenzoyloxy)ethyl group, an α-(ethoxycarbonyloxy)ethyl group, a phthalidyl group, an indanyl group, a phenyl group, an ethylphenyl group or an acetylphenyl group.

3. The 5-alkoxy-picolinic esters according to claim 1, wherein $R_1$ represents a pivaloyloxymethyl group, an α-pivaloyloxyethyl group, an acetoxymethyl group, an isobutyryloxymethyl group, an α-(isovaleroyloxy)ethyl group, an α-benzoyloxyethyl group, an α-(3,4,5-trimethoxybenzoyloxy)ethyl group, a phthalidyl group, an indanyl group, a phenyl group, an ethylphenyl group, or an acetylphenyl group.

4. The 5-alkoxy-picolinic esters according to claim 1, wherein $R_1$ represents a pivaloyloxymethyl group, a phenyl group, an ethylphenyl group, an acetylphenyl group or an indanyl group.

5. The 5-alkoxy-picolinic esters according to claim 1, wherein R represents an n-propyl group or an n-butyl group.

6. An anti-hypertensive composition containing, as an active ingredient, a therapeutically effective amount of at least one 5-alkoxy-picolinic ester represented by the formula (I):

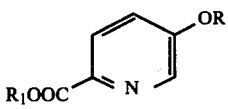

wherein R represents an alkyl group having 1 to 6 carbon atoms and $R_1$ represents a phthalidyl group; a phenyl group; an indanyl group; or an acyloxyalkyl group having the formula

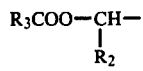

wherein $R_2$ represents a hydrogen atom or a methyl group and $R_3$ represents an alkyl group, an alkoxy group, a phenyl group or an aralkyl group.

7. The anti-hypertensive composition according to claim 6, wherein $R_1$ represents a pivaloyloxymethyl group, an α-pivaloyloxyethyl group, an acetoxymethyl group, an α-acetoxyethyl group, an α-propionyloxyethyl group, a benzoyloxymethyl group, an isobutyryloxymethyl group, an α-(isovaleroyloxy)ethyl group, an α-(benzoyloxy)ethyl group, an α-(p-methoxybenzoyloxy)ethyl group, an α-(3,5,5-trimethoxybenzoyloxy)ethyl group, an α-(ethoxycarbonyloxy)ethyl group, a phthalidyl group, an indanyl group, a phenyl group, an ethylphenyl group or an acetylphenyl group.

8. The anti-hypertensive composition according to claim 6, wherein $R_1$ represents a pivaloyloxymethyl group, an α-pivaloyloxyethyl group, an acetoxymethyl group, an isobutyryloxymethyl group, an α-(isovaleroyloxy)ethyl group, an α-benzoyloxyethyl group, an α(3,4,5-trimethoxybenzoyloxy)ethyl group, a phthalidyl group, an indanyl group, a phenyl group, an ethylphenyl group, or an acetylphenyl group.

9. The anti-hypertensive composition according to claim 6, wherein $R_1$ represents a pivaloyloxymethyl group, a phenyl group, an ethylphenyl group, an acetylphenyl group or an indanyl group.

10. The anti-hypertensive composition according to claim 6, wherein R represents an n-propyl group or an n-butyl group.

* * * * *